(12) United States Patent
Tian et al.

(10) Patent No.: US 11,874,359 B2
(45) Date of Patent: Jan. 16, 2024

(54) FAST DIFFUSION TENSOR MRI USING DEEP LEARNING

(71) Applicant: THE GENERAL HOSPITAL CORPORATION, Boston, MA (US)

(72) Inventors: Qiyuan Tian, Charlestown, MA (US); Susie Yi Huang, Boston, MA (US); Berkin Bilgic, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 108 days.

(21) Appl. No.: 17/442,817

(22) PCT Filed: Mar. 27, 2020

(86) PCT No.: PCT/US2020/025205
§ 371 (c)(1),
(2) Date: Sep. 24, 2021

(87) PCT Pub. No.: WO2020/198582
PCT Pub. Date: Oct. 1, 2020

(65) Prior Publication Data
US 2022/0179030 A1    Jun. 9, 2022

Related U.S. Application Data

(60) Provisional application No. 62/824,577, filed on Mar. 27, 2019, provisional application No. 62/969,615, filed on Feb. 3, 2020.

(51) Int. Cl.
*G01V 3/00*       (2006.01)
*G01R 33/563*     (2006.01)
(Continued)

(52) U.S. Cl.
CPC ... *G01R 33/56341* (2013.01); *G01R 33/5608* (2013.01); *G06N 3/045* (2023.01); *G06N 3/08* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 9,404,986 B2 *   8/2016  White .................... G01R 33/48
9,880,251 B2 *   1/2018  Kerins ............... G01R 33/4806
(Continued)

OTHER PUBLICATIONS

Hasan et al., Comparison of Gradient Encoding Schemes for Diffusion-Tensor MRI, Journal of Magnetic Resonance Imaging, 2001, 13:769-780.
(Continued)

*Primary Examiner* — Walter L Lindsay, Jr.
*Assistant Examiner* — Frederick WEnderoth
(74) *Attorney, Agent, or Firm* — Quarles & Brady LLP

(57) ABSTRACT

Higher quality diffusion metrics and/or diffusion-weighted images are generated from lower quality input diffusion-weighted images using a suitably trained neural network (or other machine learning algorithm). High-fidelity scalar and orientational diffusion metrics can be extracted using a theoretical minimum of a single non-diffusion-weighted image and six diffusion-weighted images, achieved with data-driven supervised deep learning. As an example, a deep convolutional neural network ("CNN") is used to map the input non-diffusion-weighted image and diffusion-weighted images sampled along six optimized diffusion-encoding directions to the residuals between the input and output high-quality non-diffusion-weighted image and diffusion-weighted images, which enables residual learning to boost the performance of CNN and full tensor fitting to generate any scalar and orientational diffusion metrics.

23 Claims, 8 Drawing Sheets

(51) Int. Cl.
    *G01R 33/56*     (2006.01)
    *G06N 3/08*      (2023.01)
    *G06N 3/045*     (2023.01)

(58) Field of Classification Search
    USPC ........................................................ 324/309
    See application file for complete search history.

(56) References Cited

U.S. PATENT DOCUMENTS

2015/0310640 A1* 10/2015 Hardy ................... G06T 7/0012
                                                          382/131
2016/0061923 A1   3/2016 Mekkaoui
2017/0052241 A1*  2/2017 Cetingul .......... G01R 33/56341

OTHER PUBLICATIONS

Mani et al., Multi-Shot Multi-Channel Diffusion Data Recovery Using Structured Low-Rank Matrix Completion, arXiv:1602.07274, Feb. 22, 2016, 31 pages.

Rajagopalan et al., A Basic Introduction to Diffusion Tensor Imaging Mathematics and Image Processing Steps, Brain Disorders & Therapy, 2017, vol. 6, Issue 2, pp. 1-7.

Tax et al., Cross-Scanner and Cross-Protocol Diffusion MRI Data Harmonisation: A Benchmark Database and Evaluation of Algorithms, NeuroImage, 2019, 195:285-299.

PCT International Search Report and Written Opinion, PCT/US2020/025205, Jun. 23, 2020, 12 pages.

\* cited by examiner

FAST DIFFUSION TENSOR MRI USING DEEP LEARNING

CROSS-REFERENCE TO RELATED APPLICATIONS

This application is a U.S. National Stage of International Application No. PCT/US2020/025205 filed Mar. 27, 2020 which claims the benefit of U.S. Provisional Patent Application Ser. No. 62/824,577, filed on Mar. 27, 2019, and entitled "FAST DIFFUSION TENSOR MRI USING DEEP LEARNING," and U.S. Provisional Patent Application Ser. No. 62/969,615, filed on Feb. 3, 2020, and entitled "FAST DIFFUSION TENSOR MRI USING DEEP LEARNING," both of which are herein incorporated by reference in their entirety.

STATEMENT REGARDING FEDERALLY SPONSORED RESEARCH

This invention was made with government support under EB015896, RR019307, N5096056, and MH111419 awarded by the National Institutes of Health. The government has certain rights in the invention.

BACKGROUND

Diffusion tensor imaging ("DTI") is a neuroimaging method for probing the microstructure of the in vivo human brain using magnetic resonance imaging ("MRI"). It has been widely adopted in clinical neuroimaging for measuring white matter integrity and tracing the white matter tracts for neurosurgical guidance. Nonetheless, DTI acquisition is relatively lengthy since many repetition times ("TRs") are needed to encode the water diffusion along different directions. At least 30 diffusion weighted images ("DWIs") along uniformly distributed encoding directions are required for a rotationally invariant estimation of fractional anisotropy ("FA"), mean diffusivity ("MD"), and primary fiber orientations. Even though the recent advances of the simultaneous multislice imaging have dramatically shortened the TR for acquiring each DWI, the minimum number of DWIs for DTI has remained unchanged.

SUMMARY OF THE DISCLOSURE

The present disclosure addresses the aforementioned drawbacks by providing a method for generating a diffusion metric from magnetic resonance image data acquired from a subject. The method includes accessing magnetic resonance image data with a computer system, wherein the magnetic resonance image data include a non-diffusion-weighted image acquired from a subject and at least six diffusion-weighted images acquired from the subject, each diffusion-weighted image corresponding to one of six different diffusion-encoding directions. A neural network is accessed with the computer system, wherein the neural network has been trained on training data to learn a mapping from lower quality diffusion-weighted images to ground-truth diffusion-weighted images. The magnetic resonance image data are input to the neural network using the computer system, generating output as residual image data that represents image differences relative to the ground-truth diffusion-weighted images. Updated diffusion-weighted images are generated by combining the at least six diffusion-weighted images and the residual image data with the computer system. A diffusion metric is then generated from the updated diffusion-weighted images using the computer system.

It is another aspect of the present disclosure to provide a method for generating at least one of diffusion metrics or diffusion-weighted images of a subject. The method includes accessing magnetic resonance image data with a computer system, wherein the magnetic resonance image data include a non-diffusion-weighted image and at least six diffusion-weighted images, each diffusion-weighted image corresponding to one of six different diffusion-encoding directions. Initial diffusion tensor elements are computed from the magnetic resonance image data by using the computer system to fit the magnetic resonance image data to a diffusion tensor model. A neural network is accessed with the computer system, where the neural network has been trained on training data to learn a mapping from lower quality diffusion tensor elements to ground-truth diffusion tensor elements. The initial diffusion tensor elements are input to the neural network using the computer system, generating output as residual diffusion tensor element data that represents diffusion tensor element differences relative to the ground-truth diffusion tensor elements. Updated diffusion tensor elements are generated by combining the initial diffusion tensor elements and the residual diffusion tensor element data with the computer system. At least one of a diffusion metric or a diffusion-weighted image is then generated from the updated diffusion tensor elements using the computer system.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
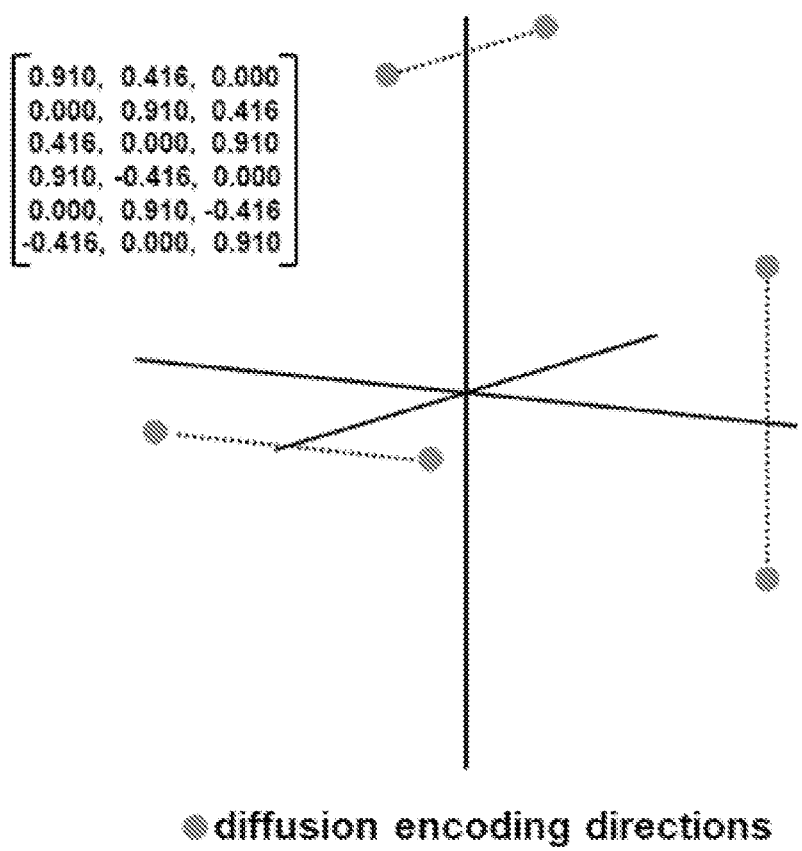
FIG. 1 shows an example of optimized diffusion-encoding directions.

Described here are systems and methods for generating higher quality diffusion metrics and/or diffusion-weighted images from lower quality input diffusion-weighted images using a suitably trained neural network (or other machine learning algorithm). The systems and methods described in the present disclosure can robustly extract high-fidelity scalar and orientational diffusion metrics using a theoretical minimum of one non-diffusion-weighted image and six diffusion-weighted images, achieved with data-driven supervised deep learning. As an example, a deep convolutional neural network ("CNN") is used to map the input non-diffusion-weighted image and diffusion-weighted images sampled along six optimized diffusion-encoding directions to the residuals between the input and output high-quality non-diffusion-weighted image and diffusion-weighted images, which enables residual learning to boost the performance of CNN and full tensor fitting to generate any scalar and orientational DTI metrics.

In some implementations, initial low-quality diffusion-weighted images are acquired, which can be acquired using optimized diffusion-encoding directions to mitigate noise. A neural network (e.g., a very deep CNN) can then be used to learn the mapping from the low-quality non-diffusion-weighted image and diffusion-weighted images to the residuals between the ground-truth high-quality non-diffusion-weighted image and diffusion-weighted images and the input low-quality non-diffusion-weighted image and diffusion-weighted images. For any incoming low-quality non-diffusion-weighted image and diffusion-weighted images, the residuals are synthesized and added to obtain high-quality non-diffusion-weighted image and diffusion-weighted images, from which diffusion metrics can be computed. Because the input non-diffusion-weighted image and diffusion-weighted images and the output ground-truth non-diffusion-weighted image and diffusion-weighted images have identical contrast, the residuals between the input and output images are sparse and contain high frequency noise and artifacts, thereby facilitating the CNN to learn a reduced amount of information.

In some other implementations, initial low-quality diffusion tensor elements are first computed from the seven input image volumes, which as noted above can in some instances be acquired using optimized diffusion-encoding directions to mitigate noise. A neural network (e.g., a very deep CNN) can then be used to learn the mapping from the low-quality non-diffusion-weighted image and diffusion tensor elements to the residuals between the ground-truth high-quality non-diffusion-weighted image and diffusion tensor elements and the input low-quality non-diffusion-weighted image and diffusion tensor elements. For any incoming low-quality non-diffusion-weighted image and diffusion tensor elements, the residuals are synthesized and added to obtain high-quality non-diffusion-weighted image and diffusion tensor elements, which are then used to derive diffusion metrics.

In either of these implementations, the systems and methods described in the present disclosure are able to obtain both the scalar (e.g., fractional anisotropy, mean diffusivity) and orientational (primary eigenvector) diffusion metrics, which differs from other techniques that can only estimate scalar diffusion metrics.

Using the methods described in the present disclosure, the acquisition of diffusion-weighted image data can be accelerated without compromising accuracy of the DTI estimates. For instance, a 15-fold acceleration can be achieved in some implementations. Advantageously, this acceleration without loss of image quality enables more feasible whole-brain diffusion tractography using a 30-60 second scan. These reductions in DTI scan time are particularly advantageous for clinical applications such as DTI tractography on radiological, neurological, neurosurgical, psychiatric, and psychological research and/or health care.

The methods described in the present disclosure can also be implemented with minimal training data, and can be easily generalized and deployed on any arbitrary MRI scanner.

In a Stejskal-Tanner PGSE sequence, the measured diffusion signal intensity $S_i$ (i=1, 2, ..., N) in a brain voxel is given by:

$$S_i = S_0 e^{-b_i \cdot g_i^T \cdot D \cdot g_i}; \qquad (1)$$

where $S_0$ is the measured signal intensity in the absence of diffusion-encoding gradient, b is a scalar value representing the diffusion-encoding strength (often referred to as the b-value), $g_i=(g_{ix},g_{iy},g_{iz})^T$ is a unit column vector representing the diffusion-encoding direction, and D is a 3×3 symmetric matrix with six unique elements representing a diffusion tensor that can be given as:

$$D = \begin{bmatrix} D_{xx} & D_{xy} & D_{xz} \\ D_{xy} & D_{yy} & D_{yz} \\ D_{xz} & D_{yz} & D_{zz} \end{bmatrix}. \qquad (2)$$

The diffusion tensor, D, is the 3D covariance matrix of the displacements in a given time during which the water molecules are allowed to displace. Specifically, the diagonal elements of D correspond to the apparent diffusion coefficients ("ADCs") along three orthogonal axes in the MRI scanner measurement frame, while the off-diagonal elements correspond to the correlation between displacements along those orthogonal axes. The diffusion tensor, D, can be diagonalized using eigen decomposition as:

$$D = \begin{bmatrix} v_1 & v_2 & v_3 \end{bmatrix} \begin{bmatrix} \lambda_1 & 0 & 0 \\ 0 & \lambda_2 & 0 \\ 0 & 0 & \lambda_3 \end{bmatrix} \begin{bmatrix} v_1^T \\ v_2^T \\ v_3^T \end{bmatrix}; \qquad (3)$$

where $v_1$, $v_2$, and $v_3$ are the eigenvectors representing the three principal axes of the eigen system; and $\lambda_1$, $\lambda_2$, and $\lambda_3$ are the eigenvalues representing the ADCs along $v_1$, $v_2$, and $v_3$. Several metrics can be derived to quantitatively characterize microstructural properties, including the following:

Axial diffusivity $(AD) = \lambda_1$

Radial diffusivity $(RD) = \dfrac{(\lambda_2 + \lambda_3)}{2}$

Mean diffusivity $(MD) = \dfrac{(\lambda_1 + \lambda_2 + \lambda_3)}{3}$

Fractional anisotrophy $(FA) =$ $$\sqrt{\frac{3}{2} \frac{\sqrt{(\lambda_1 - MD)^2 + (\lambda_2 - MD)^2 + (\lambda_3 - MD)^2}}{2\sqrt{\lambda_1^2 + \lambda_2^2 + \lambda_3^2}}}.$$

For neuroimaging applications, the primary eigenvector $v_1$ indicates the local axon fiber orientation in the white matter, which can be used for diffusion tractography to reconstruct the 3D computational model of white matter pathways.

To solve for a diffusion tensor, D, Eqn. (1) can be rewritten as:

$$ADC_i = \frac{-\ln(S_i/S_0)}{b_i} = g_i^T \cdot D \cdot g_i; \qquad (4)$$

where $ADC_i$ is the ADC derived from measurement $S_i$. The term $g_i^T \cdot D \cdot g_i$ can be represented in a matrix formalism as, $$g_i^T \cdot D \cdot g_i = \begin{bmatrix} g_{ix}^2 & g_{iy}^2 & g_{iz}^2 & 2g_{ix}g_{iy} & 2g_{ix}g_{iz} & 2g_{iy}g_{iz} \end{bmatrix} \begin{bmatrix} D_{xx} \\ D_{yy} \\ D_{zz} \\ D_{xy} \\ D_{xz} \\ D_{yz} \end{bmatrix} = \alpha_i^T X. \qquad (5)$$

Substituting Eqn. (5) in Eqn. (4) provides:

$$ADC = AX; \qquad (6)$$

where $A = [\alpha_1 \; \alpha_2 \; \ldots \; \alpha_N]^T$ is solely dependent on the diffusion-encoding directions and is often referred to as the transformation matrix for the corresponding diffusion-encoding scheme, and X is an unknown vector of diffusion tensor elements to be solved.

For six independent ADC measurements along non-collinear directions (i.e., N=6), X can be simply solved as:

$$X = A^{-1} ADC. \qquad (7)$$

For an optimized selection of diffusion-encoding directions, such as those shown in FIG. 1, the inversion of the transformation matrix A is well-conditioned (e.g., condition number as low as 1.3228), which improves the robustness of X to the noise in the ADC measurement. For more than six measurements, Eqn. (6) can be solved using ordinary least squares and other methods. For less than six measurements, Eqn. (6) is underdetermined with many solutions.

When the b-value of the non-diffusion weighted signal is not exactly zero because of diffusion-encoding gradient nonlinearity and/or spoiler gradients in the PGSE sequence, for improved accuracy, Eon. (1) can be rewritten as:

$$\begin{aligned} \ln(S_i) &= \ln(S_0) - b_i \alpha_i^T X \\ &= \begin{bmatrix} -b_i g_{ix}^2 & -b_i g_{iy}^2 & -b_i g_{iz}^2 & -2b_i g_{ix} g_{iy} & -2b_i g_{ix} g_{iz} & -2b_i g_{iy} g_{iz} & 1 \end{bmatrix} \begin{bmatrix} D_{xx} \\ D_{yy} \\ D_{zz} \\ D_{xy} \\ D_{xz} \\ D_{yz} \\ 1 \end{bmatrix} \\ &= \beta_i^T X \end{aligned} \qquad (8)$$

or in matrix form as:

$$\ln(S) = BY; \quad (9)$$

where $B=[\beta_1\ \beta_2\ \ldots\ \beta_N]^T$. The matrix Y can be solved for as:

$$Y = B^{-1}\ln(S). \quad (10)$$

Figure 2:
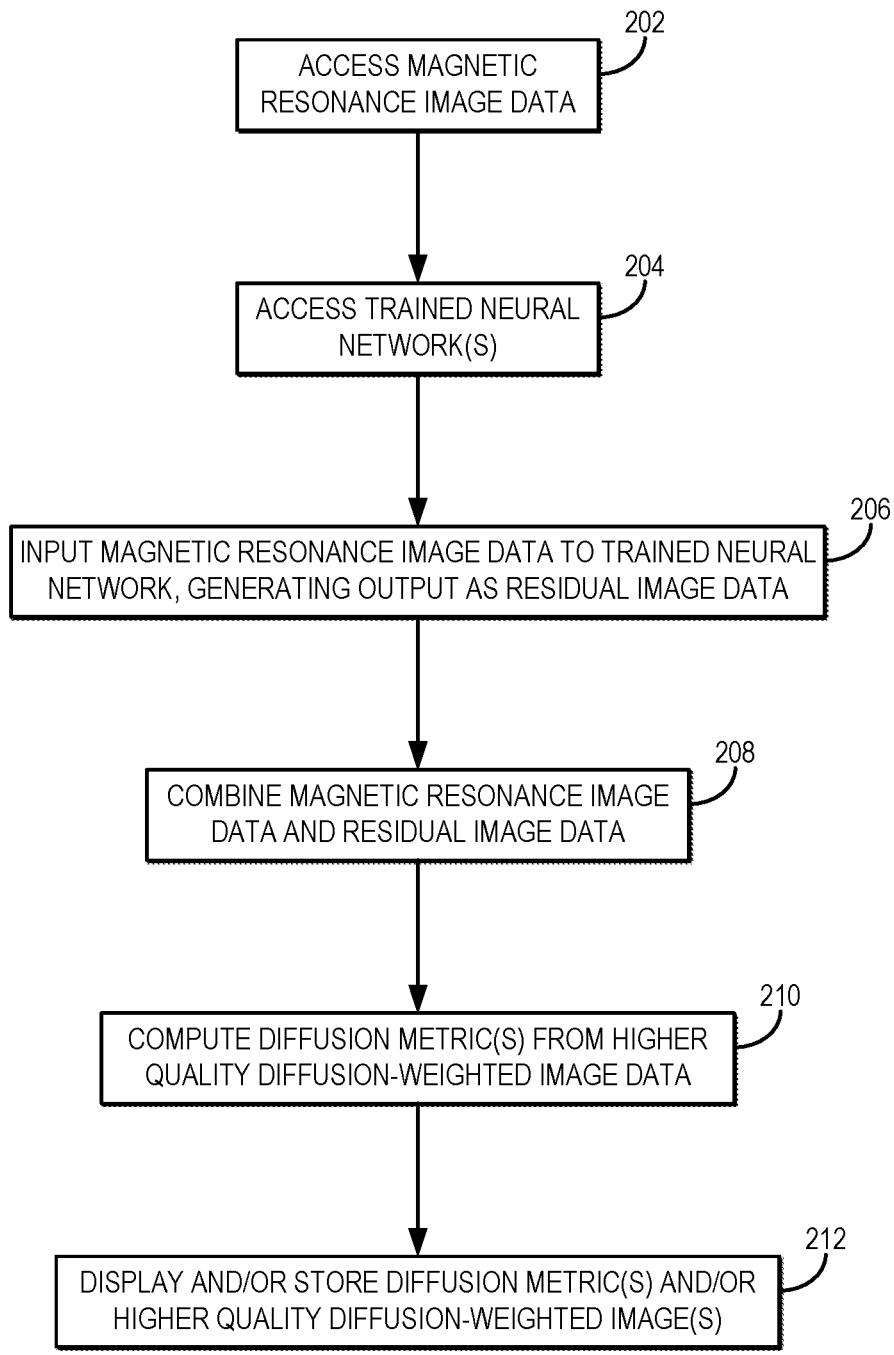
FIG. 2 is a flowchart setting forth the steps of an example method for generating diffusion metrics and/or high-quality diffusion-weighted images from low-quality input diffusion-weighted images using a neural network that has been trained to learn a mapping between low-quality diffusion-weighted images to residuals relative to ground-truth diffusion-weighted images.

Referring now to FIG. 2, a flowchart is illustrated as setting forth the steps of an example method for using a suitably trained neural network or other machine learning algorithm to generate higher quality diffusion metrics and/or diffusion-weighted images than otherwise attainable from the available magnetic resonance image data.

The method includes accessing magnetic resonance image data with a computer system, as indicated at step 202. Accessing the magnetic resonance image data may include retrieving such data from a memory or other suitable data storage device or medium. Alternatively, accessing the magnetic resonance image data may include acquiring such data with an MRI system and transferring or otherwise communicating the data to the computer system, which may be a part of the MRI system. The magnetic resonance image data preferably includes reconstructed images, but in some instances may include k-space data from which images can be reconstructed.

As one example, the magnetic resonance image data include a single non-diffusion-weighted image (i.e., a b=0 image) or image volume; six diffusion-weighted images or image volumes, each sampled along a different diffusion-encoding direction that is preferably an optimized diffusion-encoding direction; and one or more anatomical images or image volumes. The magnetic resonance image data may also include more than six diffusion-weighted images or image volumes (e.g., corresponding to diffusion encoding along more than six directions). The anatomical images may include, for instance, a T1-weighted image, a T2-weighted image, or both.

The optimized diffusion-encoding directions can be selected to minimize the condition number of the diffusion tensor transformation matrix, which defines the linear mapping between the diffusion tensor elements and the diffusivity estimates derived from the diffusion-weighted signals. An example of six optimized diffusion-encoding directions is illustrated in FIG. 1. In other implementations, the optimized diffusion-encoding directions can include more than six diffusion-encoding directions that minimize the condition number of the diffusion tensor transformation matrix. Anatomical images can be included as inputs because they are routinely acquired and help delineate boundaries between anatomical structures while preventing blurring in the results.

The use of optimized diffusion-encoding directions (e.g., six optimized diffusion-encoding directions) that minimize the condition number of the diffusion tensor transformation matrix provides a number of advantages for the methods described in the present disclosure. As one advantage, the use of the optimized diffusion-encoding directions improves the robustness of diffusion tensor fitting of the resultant images to any imperfection introduced by the neural network(s).

As another advantage, using the optimized diffusion-encoding directions allows for training data to be extracted from a routinely acquired single-shell multi-directional diffusion dataset, making it easy to acquire and process new training data or use legacy data as training data. For instance, the input diffusion-weighted images can be transformed from the diffusion-weighted images sampled along rotational variations of the optimized diffusion-encoding directions without amplifying experimental noise and artifacts. Such transformed images have the same image contrast as the ground-truth images, but with different observed noise characteristics and artifacts. For example, ground-truth diffusion-weighted images can be generated by fitting the tensor model to all available b=0 images and diffusion-weighted images to generate diffusion tensor elements, and then inverting the diffusion tensor transformation to generate from those diffusion tensor elements, a set of diffusion-weighted images sampled along the optimized diffusion-encoding directions.

A trained neural network (or other suitable machine learning algorithm) is then accessed with the computer system, as indicated at step 204. Accessing the trained neural network may include accessing network parameters (e.g., weights, biases, or both) that have been optimized or otherwise estimated by training the neural network on training data. In some instances, retrieving the neural network can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

Instead of directly learning DTI metrics as in previous works, the neural network is trained, or has been trained, on training data in order to learn the residuals between input and output non-diffusion-weighted image and diffusion-weighted images (e.g., the residuals between lower quality non-diffusion-weighted image and diffusion-weighted images and higher quality ground-truth non-diffusion-weighted image and diffusion-weighted images).

Figure 4:
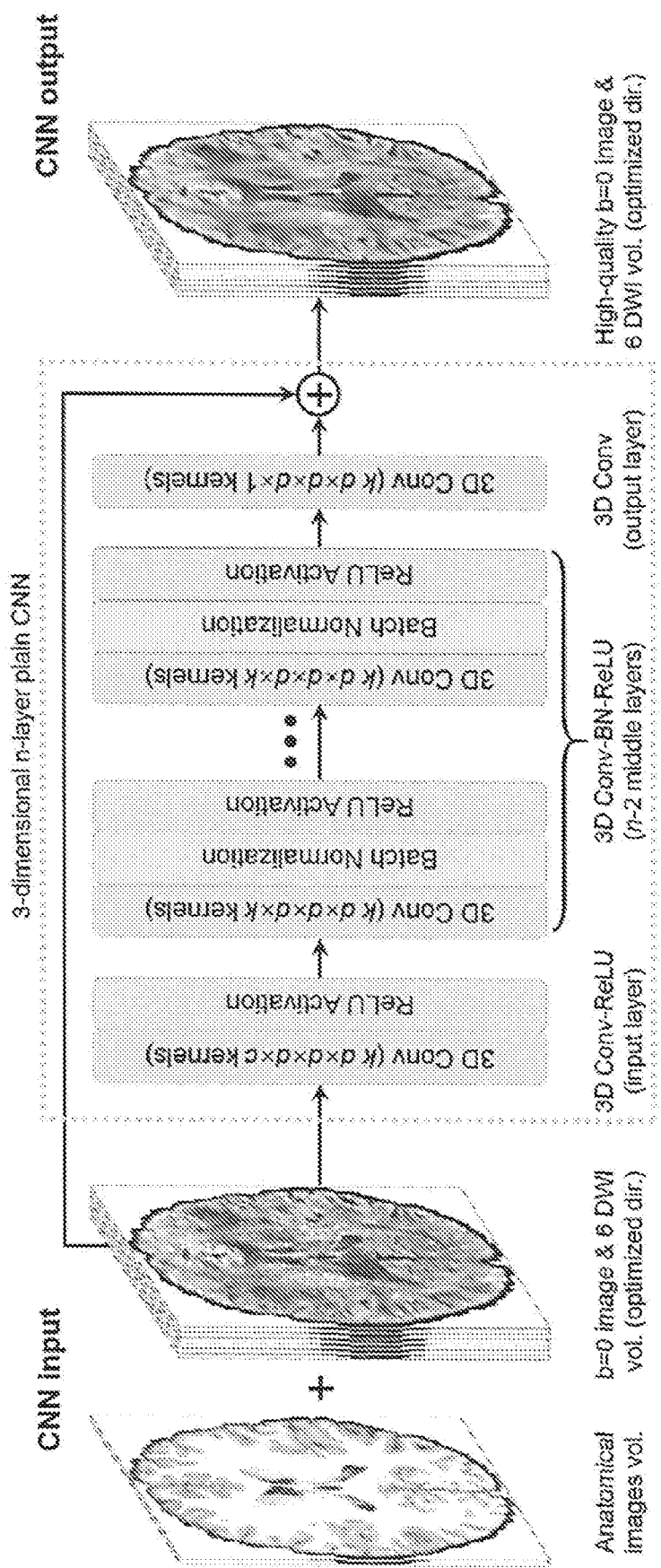
FIG. 4 is an example neural network architecture that can be implemented in some embodiments described in the present disclosure.

An example of a neural network that can be trained in this manner is shown in FIG. 4. This example neural network includes a three-dimensional convolutional neural network ("CNN") that is trained to learn the mapping from the input image volumes to the residuals between the input and output non-diffusion-weighted image and diffusion-weighted image volumes, which may be encoded along optimized diffusion-encoding directions. The network architecture of the CNN includes stacked convolutional filters paired with batch normalization functions and non-linear activation functions (e.g., rectified linear units or other suitable activation functions). The plain network coupled with residual learning is effective for image de-noising and super-resolution.

The magnetic resonance image data are then input to the one or more trained neural networks, generating output as residual image data, as indicated at step 206. Higher quality non-diffusion-weighted image and diffusion-weighted image data are then generated by combining the "low-quality" magnetic resonance image data with the residual image data, as indicated at step 208.

From the higher quality non-diffusion-weighted image and diffusion-weighted image data, one or more diffusion metrics can be computed, as indicated at step 210. The diffusion metrics can be scalar diffusion metrics, orientational diffusion metrics, or both. For example, an axial diffusivity ("AD") metric can be computed. As another example, a radial diffusivity ("RD") metric can be computed. As still another example, a mean diffusivity ("MD") metric can be computed. The computed diffusion metric(s) may also include fraction anisotropy ("FA").

Additionally or alternatively, the diffusion metric(s) may include one or more eigenvectors or eigenvalues computed from the diffusion tensor constructed from the higher quality diffusion tensor elements. For instance, the diffusion metric(s) may include the principal eigenvector, $v_1$, which may be used for fiber tractography applications.

The diffusion metric(s) and/or higher quality non-diffusion-weighted image and/or diffusion-weighted images can then be displayed to a user, stored for later use or further processing, or both, as indicated at step 214. For instance, parameter maps can be generated for the computed diffusion metrics and displayed to a user. As an example, an AD map, an RD map, an MD map, and/or an FA map can be generated to depict the spatial distribution of these diffusion metrics in the subject.

Figure 3:
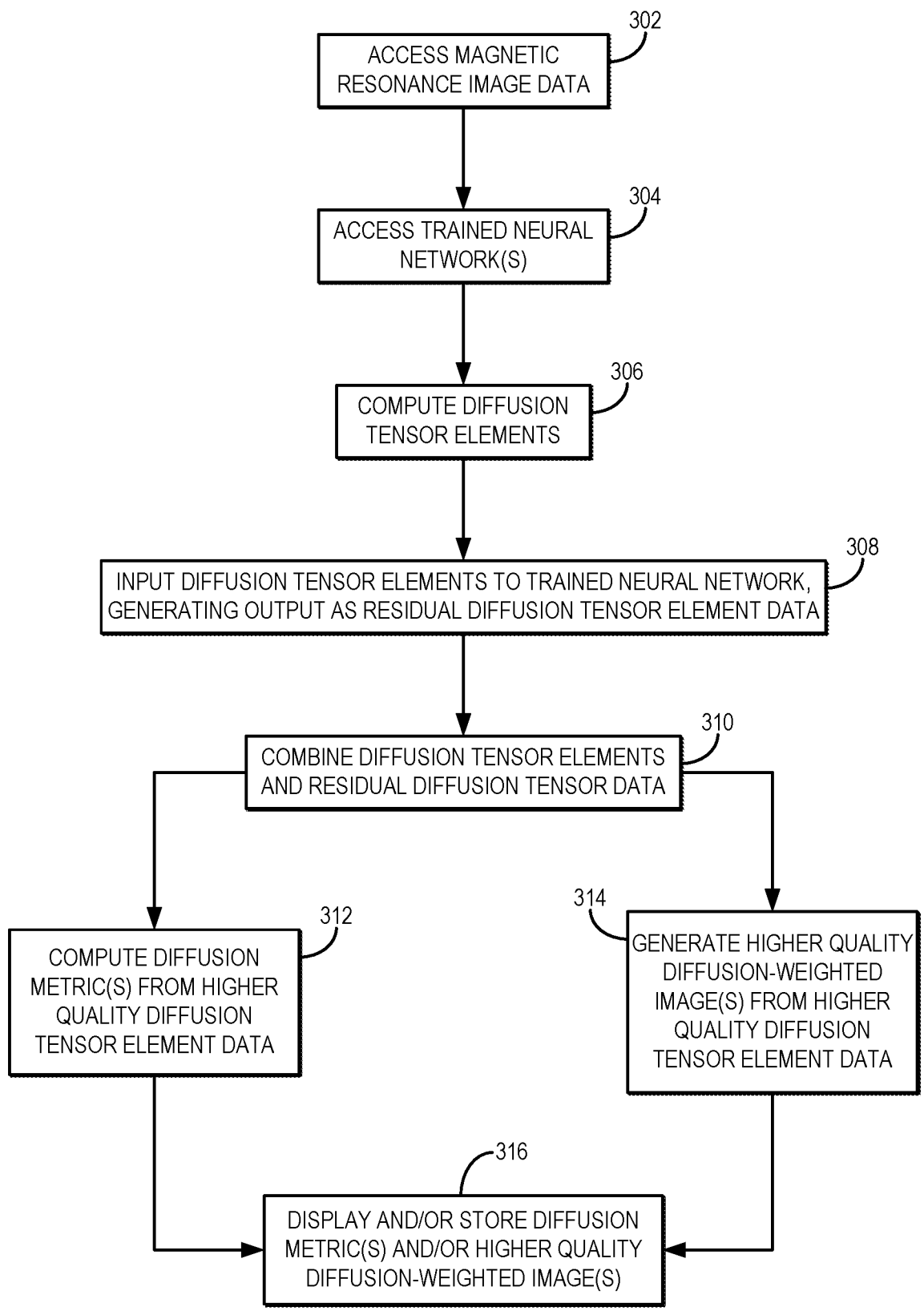
FIG. 3 is a flowchart setting forth the steps of an example method for generating diffusion metrics and/or high-quality diffusion-weighted images from low-quality input diffusion-weighted images using a neural network that has been trained to learn a mapping between diffusion tensor elements computed from low-quality diffusion-weighted images to residuals relative to ground-truth diffusion tensor element data.

Referring now to FIG. 3, a flowchart is illustrated as setting forth the steps of an example method for using a suitably trained neural network or other machine learning algorithm to generate higher quality diffusion metrics and/or non-diffusion-weighted image and diffusion-weighted images than otherwise attainable from the available magnetic resonance image data.

The method includes accessing magnetic resonance image data with a computer system, as indicated at step 302. Accessing the magnetic resonance image data may include retrieving such data from a memory or other suitable data storage device or medium. Alternatively, accessing the magnetic resonance image data may include acquiring such data with an MRI system and transferring or otherwise communicating the data to the computer system, which may be a part of the MRI system. The magnetic resonance image data preferably includes reconstructed images, but in some instances may include k-space data from which images can be reconstructed.

As one example, the magnetic resonance image data include a single non-diffusion-weighted image (i.e., a b=0 image) or image volume; six diffusion-weighted images or image volumes, each sampled along a different diffusion-encoding direction that is preferably an optimized diffusion-encoding direction; and one or more anatomical images or image volumes. The magnetic resonance image data may also include more than six diffusion-weighted images or image volumes (e.g., corresponding to diffusion encoding along more than six directions). The anatomical images may include, for instance, a T1-weighted image, a T2-weighted image, or both.

The optimized diffusion-encoding directions can be selected to minimize the condition number of the diffusion tensor transformation matrix, which defines the linear mapping between the diffusion tensor elements and the diffusivity estimates derived from the diffusion-weighted signals. An example of six optimized diffusion-encoding directions is illustrated in FIG. 1. In other implementations, the optimized diffusion-encoding directions can include more than six diffusion-encoding directions that minimize the condition number of the diffusion tensor transformation matrix. Anatomical images can be included as inputs because they are routinely acquired and help delineate boundaries between anatomical structures while preventing blurring in the results.

The use of optimized diffusion-encoding directions (e.g., six optimized diffusion-encoding directions) that minimize the condition number of the diffusion tensor transformation matrix provides a number of advantages for the methods described in the present disclosure. As one advantage, the use of the optimized diffusion-encoding directions improves the robustness of diffusion tensor fitting of the resultant images to any imperfection introduced by the neural network(s).

As another advantage, using the optimized diffusion-encoding directions allows for training data to be extracted from a routinely acquired single-shell multi-directional diffusion dataset, making it easy to acquire and process new training data or use legacy data as training data. For instance, the input diffusion tensor elements can be computed from the diffusion-weighted images sampled along rotational variations of the optimized diffusion-encoding directions without amplifying experimental noise and artifacts. Such diffusion tensor elements have the same image contrast as the ground-truth diffusion tensor elements, but with different observed noise characteristics and artifacts. For example, ground-truth diffusion-weighted images can be generated by fitting the tensor model to all available b=0 images and diffusion-weighted images to generate diffusion tensor elements.

A trained neural network (or other suitable machine learning algorithm) is then accessed with the computer system, as indicated at step 304. Accessing the trained neural network may include accessing network parameters (e.g., weights, biases, or both) that have been optimized or otherwise estimated by training the neural network on training data. In some instances, retrieving the neural network can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

Instead of directly learning DTI metrics as in previous works, the neural network is trained, or has been trained, on training data in order to learn the residuals between input and output non-diffusion-weighted image and diffusion tensor elements (e.g., the residuals between diffusion tensor elements computed from the input non-diffusion-weighted image and diffusion-weighted images and diffusion tensor elements computed from higher quality ground-truth non-diffusion-weighted image and diffusion-weighted images).

Figure 5:
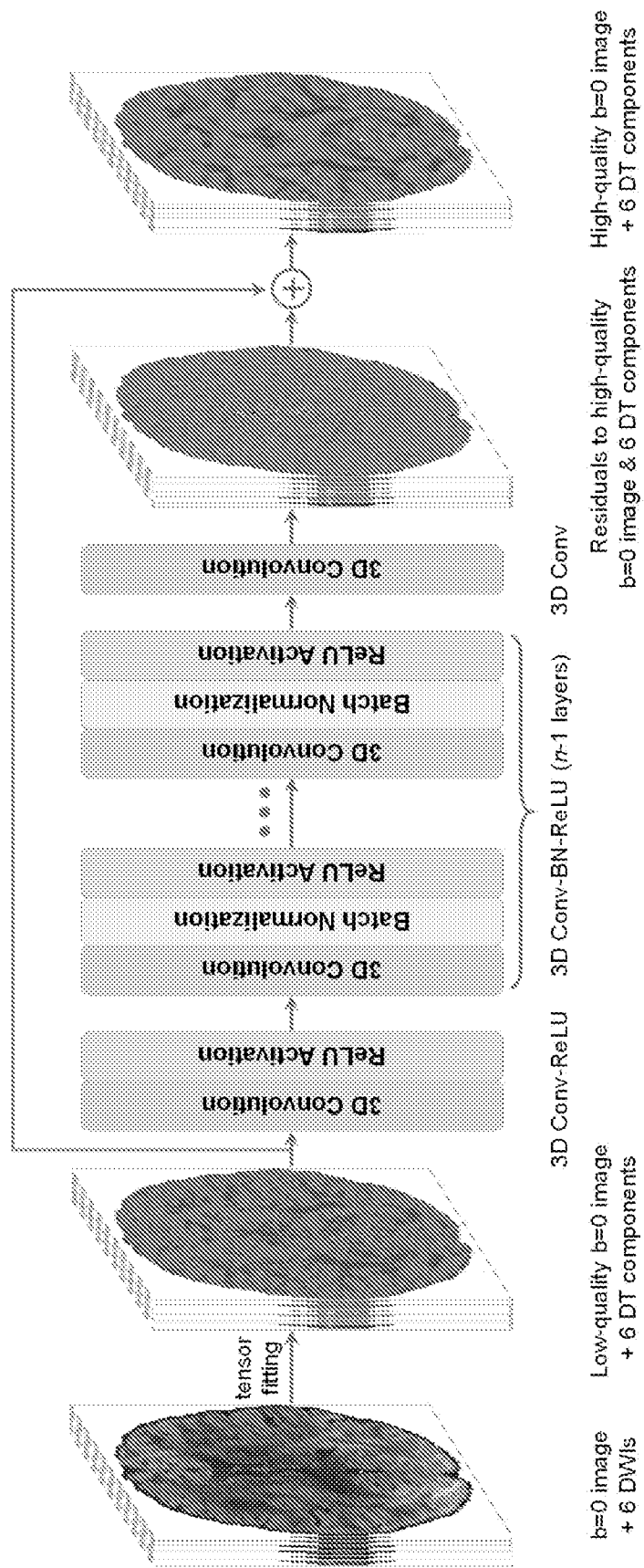
FIG. 5 is another example neural network architecture that can be implemented in some embodiments described in the present disclosure.

An example of a neural network that can be trained in this manner is shown in FIG. 5. This example neural network includes a three-dimensional convolutional neural network ("CNN") that is trained to learn the mapping from the input non-diffusion-weighted image and diffusion tensor elements to the residuals between the input and output non-diffusion-weighted image and diffusion tensor elements. The network architecture of the CNN includes stacked convolutional filters paired with batch normalization functions and non-linear activation functions (e.g., rectified linear units or other suitable activation functions). The plain network coupled with residual learning is effective for image de-noising and super-resolution.

Diffusion tensor elements are then computed from the magnetic resonance image data, as indicated at step 306. For example, the diffusion tensor elements can be computed using the diffusion tensor model fitting techniques described above. Alternatively, other methods for computing diffusion tensor elements can be implemented. In general, these diffusion tensor elements will be "low-quality" because they are computed from a single non-diffusion-weighted image and diffusion-weighted images obtained using the mathematical minimum of six diffusion-encoding directions. In other instances, the low-quality diffusion-weighted images may include more than six diffusion-weighted images (e.g., corresponding to diffusion encoding along more than six directions).

The non-diffusion-weighted image and diffusion tensor elements are then input to the one or more trained neural networks, generating output as residual non-diffusion-weighted image and diffusion tensor element data, as indicated at step 308.

Higher quality non-diffusion-weighted image and diffusion tensor elements are then generated by combining the "low-quality" non-diffusion-weighted image and diffusion tensor elements with the residual non-diffusion-weighted image and diffusion tensor element data, as indicated at step 310.

From the higher quality diffusion tensor elements, one or more diffusion metrics can be computed, as indicated at step 312. The diffusion metrics can be scalar diffusion metrics, orientational diffusion metrics, or both. For example, an axial diffusivity ("AD") metric can be computed. As another example, a radial diffusivity ("RD") metric can be computed. As still another example, a mean diffusivity ("MD") metric can be computed. The computed diffusion metric(s) may also include fraction anisotropy ("FA").

Additionally or alternatively, the diffusion metric(s) may include one or more eigenvectors or eigenvalues computed from the diffusion tensor constructed from the higher quality diffusion tensor elements. For instance, the diffusion metric(s) may include the principal eigenvector, $v_1$, which may be used for fiber tractography applications.

Additionally or alternatively, higher quality diffusion-weighted images can be generated from the higher quality diffusion tensor elements, as indicated at step 314. For example, an inverse of the diffusion tensor transformation can be applied to the higher quality diffusion tensor elements in order to reconstruct the underlying, higher quality diffusion-weighted images.

The diffusion metric(s) and/or higher quality diffusion-weighted images can then be displayed to a user, stored for later use or further processing, or both, as indicated at step 316. For instance, parameter maps can be generated for the computed diffusion metrics and displayed to a user. As an example, an AD map, an RD map, an MD map, and/or an FA map can be generated to depict the spatial distribution of these diffusion metrics in the subject.

As noted above, an example of neural networks that can be used to implement the methods described in the present disclosure is shown in FIGS. 4 and 5. The neural network in FIG. 4 has been trained to learn the residual between input and output non-diffusion-weighted image and diffusion-weighted images, and the neural network in FIG. 5 has been trained to learn the residual between input and output non-diffusion-weighted image and diffusion tensor elements. In some instances, the neural network can be a convolutional neural network ("CNN"). As one non-limiting example, the CNN could be a CNN with a U-Net architecture. As another example, the neural network can be a residual neural network, which may in some instances be a residual CNN. Furthermore, the neural network can be a two-dimensional neural network or a three-dimensional neural network. Other suitable neural network architectures can also be used, as will be appreciated by those skilled in the art.

The neural networks can be, for example, a 3D CNN, which is trained to learn the mapping from low-quality diffusion-weighted images or diffusion tensor elements and a single b=0 image to their residuals to the high-quality diffusion-weighted images or diffusion tensor elements from a longer acquisition and the averaged b=0 image. As shown in FIGS. 4 and 5, the neural networks can use a plain network architecture, which is characterized by its simplicity.

The input of these example neural networks is the low-quality diffusion-weighted images or diffusion tensor elements and a single b=0 image. The output of these example neural networks is the residuals between the low-quality diffusion-weighted images or diffusion tensor elements and single b=0 image and the high-quality diffusion-weighted images or diffusion tensor elements and the averaged b=0 image. The neural networks include one input layer of 3D convolution and rectified linear unit (ReLU) nonlinear activation, n−2 middle layers of paired 3D convolution, batch normalization (BN) and ReLU activation, and a final 3D convolutional layer. Thus, a 20-layer implementation will have 18 middle layers. As an example, the input layer can have 64 kernels with a size of 3×3×3×7. Each of the middle layers can have 64 kernels with a size 3×3×3×64. The output layer can have seven kernels with a size of 3×3×3×64. The output layer can exclude ReLU activation such that the output includes both positive and negative values.

Figure 6:
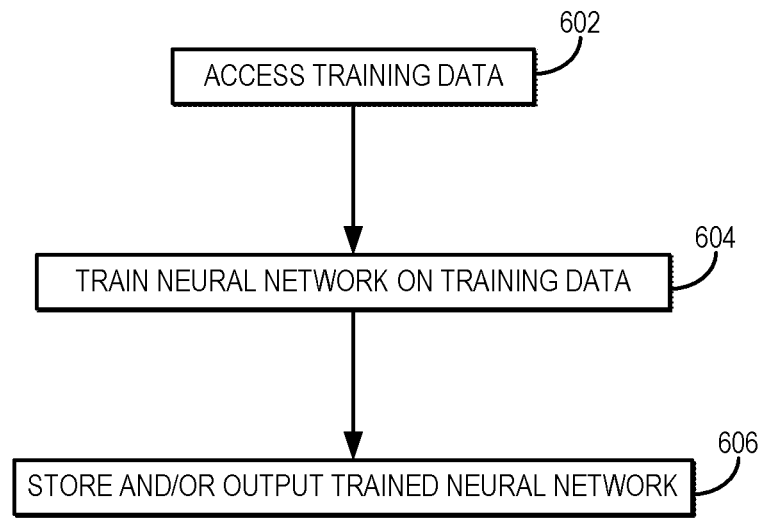
FIG. 6 is a flowchart setting forth the steps of an example method for training a neural network in accordance with some embodiments described in the present disclosure.

Referring now to FIG. 6, a flowchart is illustrated as setting forth the steps of an example method for training one or more neural networks (or other suitable machine learning algorithms) on training data, such that the one or more neural networks are trained to receive input as diffusion tensor elements in order to generate output as residual diffusion tensor element data.

In general, the neural network(s) can implement any number of different neural network architectures. For instance, the neural network(s) could implement a convolutional neural network, a residual neural network, and so on. In some instances, the neural network(s) may implement deep learning. Alternatively, the neural network(s) could be replaced with other suitable machine learning algorithms, such as those based on supervised learning, unsupervised learning, deep learning, ensemble learning, dimensionality reduction, and so on.

The method includes accessing training data with a computer system, as indicated at step 602. Accessing the training data may include retrieving such data from a memory or other suitable data storage device or medium. Alternatively, accessing the training data may include acquiring such data with an MRI system and transferring or otherwise communicating the data to the computer system, which may be a part of the MRI system. In general, the training data can include magnetic resonance image data that include non-diffusion-weighted images (e.g., b=0 images) and a number of diffusion-weighted images ("DWIs").

Additionally or alternatively, the method can include assembling training data from magnetic resonance image data using the computer system. This step may include assembling the magnetic resonance image data into an appropriate data structure on which the machine learning algorithm can be trained. Assembling the training data may include assembling non-diffusion-weighted image data, diffusion-weighted image data, and/or diffusion tensor element data. For example, as described above, ground-truth diffusion-weighted images can be generated by fitting the tensor model to all available b=0 images and diffusion-weighted images to generate diffusion tensor elements, and then inverting the diffusion tensor transformation to generate from those diffusion tensor elements, a set of diffusion-weighted images sampled along the optimized diffusion-encoding directions.

As one non-limiting example, the training data may include 90 diffusion-weighted images and 18 b=0 images. In some instances, assembling the training data may include computing an average b=0 image from the available b=0 images. Assembling the training data may also include resampling diffusion-weighted images along the optimized diffusion-encoding directions.

When learning the residuals in the diffusion tensor space, to obtain ground-truth high-quality diffusion tensor elements and diffusion metrics, a diffusion tensor model can be fitted on the 18 b=0 images and 90 DWIs. The b-values and b-vectors can be corrected during the fitting process to account for the gradient non-linearity.

As one example, to obtain input images and/or diffusion tensor elements, DWIs along six encoding directions were selected out of the 90 DWIs with one b=0 image randomly selected from the 18 b=0 images. DWI were selected approximately along the six optimized diffusion-encoding directions or their rotations. For each selected set, the maximum angle between an ideal and acquired encoding direction was limited to less than 10 degrees. For a total number of 90 diffusion-encoding directions, approximately 70 sets of six DWIs can be selected. The diffusion tensor model was fitted following Eqn. (10) with corrected b-values and b-vectors.

To account for subject-to-subject variations in image intensity, the intensities of the input and ground-truth images can also be standardized by subtracting the mean image intensity and dividing by the standard deviation of image intensities across all voxels within a brain mask from the input images. Input and ground-truth images can also be brain masked.

One or more neural networks (or other suitable machine learning algorithms) are trained on the training data, as indicated at step 604. In general, the neural network can be trained by optimizing network parameters (e.g., weights, biases, or both) based on minimizing a loss function. As one non-limiting example, the loss function may be a mean squared error loss function. For instance, a mean-square-error (L2) loss compared to the ground-truth can be used to optimize the network parameters using an Adam optimizer. In some implementations, only the mean-square-error within a brain masked region can be used.

Training a neural network may include initializing the neural network, such as by computing, estimating, or otherwise selecting initial network parameters (e.g., weights, biases, or both). Training data can then be input to the initialized neural network, generating output as residual non-diffusion-weighted image and diffusion-weighted image data or residual non-diffusion-weighted image and diffusion tensor element data. The quality of the output can then be evaluated, such as by passing the output to the loss function to compute an error. The current neural network can then be updated based on the calculated error (e.g., using backpropagation methods based on the calculated error). For instance, the current neural network can be updated by updating the network parameters (e.g., weights, biases, or both) in order to minimize the loss according to the loss function. When the error has been minimized (e.g., by determining whether an error threshold or other stopping criterion has been satisfied), the current neural network and its associated network parameters represent the trained neural network.

In one non-limiting example, training was performed on 40 subjects and validated on another 10 subjects using a GPU for 36 epochs at a learning rate of 0.0005 and for 12 epochs at a learning rate of 0.00001 (~70 hours in total). Blocks of 64×64×64 voxel size were used for training (8 blocks from each subject). The learned network parameters were applied to the whole brain volume of each of the evaluation subjects.

The one or more trained neural networks are then stored for later use, as indicated at step 606. Storing the neural network(s) may include storing network parameters (e.g., weights, biases, or both), which have been computed or otherwise estimated by training the neural network(s) on the training data. Storing the trained neural network(s) may also include storing the particular neural network architecture to be implemented. For instance, data pertaining to the layers in the neural network architecture (e.g., number of layers, type of layers, ordering of layers, connections between layers, hyperparameters for layers) may be stored.

A supervised machine learning approach to estimate both scalar and orientational DTI metrics from a single b=0 image and six or more DWIs selected along optimal diffusion-encoding directions has been described. In some implementations, the method first estimates low-quality diffusion tensor elements from the input images and learns the mapping from the input b=0 image and low-quality diffusion tensor elements to their residuals relative to the high-quality b=0 image and diffusion tensor elements using a deep CNN. In other implementations, the residuals between the low-quality non-diffusion-weighted image and diffusion-weighted images and the high-quality non-diffusion-weighted image and diffusion-weighted images are instead learned and output. The output data are similar in quality to those from a 15-fold longer data acquisition.

Advantageously, the methods described in the present disclosure are able to recover high-quality diffusion tensor data from the theoretical minimum data requirement (i.e., six different diffusion-encoding directions), which enables the reconstruction of whole brain white matter pathways for a wide variety of clinical and neuroscientific applications with a significantly reduced data acquisition burden.

A notable advantage of the methods described in the present disclosure is their simplicity and practicality. As one example, the approach can use images obtained from the MRI scanner as input. As a result, the approach can be deployed as a stand-alone post-processing software package or incorporated into an existing software package, such as DTI-based tractography software for surgical planning.

As still another example, the DTI scan time reduction attainable when using the methods described in the present disclosure not only increases throughput and comfort while reducing cost, but also enables advanced tractography-based analyses in previously inaccessible populations, such as motion-prone patients and young children. The described approach, coupled with techniques for quantifying diffusion MRI metrics along white matter bundles (e.g., automated fiber quantification), could help to evaluate alterations in tissue microstructure along white matter bundles more precisely and provide greater tract specificity in studies of white matter plasticity, degeneration, and maturation.

The systems and methods described in the present disclosure also enable a number of advantages. First, learning the residuals is much simpler than explicitly synthesizing the ground-truth, since the input low-quality b=0 image and diffusion-weighted images and/or diffusion tensor elements share the same information to a large extent with the ground-truth b=0 image and diffusion-weighted images and/ or diffusion tensor elements. Residual learning emphasizes optimized selection of the input DWIs that minimizes the residuals between the inputs and the ground-truth. An optimized set of diffusion-encoding directions that minimizes the condition number of the DTI transformation matrix (Eqn. (7)) can be used. The synergistic combination of diffusion MRI physics and residual learning further boosts the performance of the methods described in the present disclosure.

Second, recovery of the orientational information, such as the primary eigenvector for diffusion tractography, is possible. Previous deep-learning approaches have only attempted to estimate the scalar metrics (e.g., fractional anisotropy) and other microstructural metrics from advanced diffusion models. Diffusion tractography remains one of the most clinically relevant and significant applications of DTI. For example, FDA-approved tractography software for neurosurgical planning (e.g., for tumor resection, deep brain stimulation, MRI-guided focused ultrasound) are based on DTI for estimating local fiber orientations. The ability of the methods described in the present disclosure to recover orientational information based on inputting magnetic resonance image data to a trained neural network is a notable improvement over existing machine learning approaches for diffusion MRI.

Third, joint 6D reconstruction of spatial and diffusion space information can be provided. In some example configurations, the convolution kernels in neural network have a size of 3×3×3×the number of b=0 images plus the number of diffusion-weighted images or diffusion tensor elements in the input layers (or number of features in the middle layers). Each of these kernels attempts to aggregate useful information from a small local neighborhood in space and all diffusion-weighted image and/or diffusion tensor/feature channels. Previous studies imposed a local sparsity constraint to recover the required information, but the methods described in the present disclosure can improve upon these previous works by increasing the extent of the spatial neighborhood to use non-local information. For example, in one configuration the receptive field of the neural network can be 41×41×41, which for some data types can be 5 mm×5 mm×5 mm. The neural networks described in the present disclosure also exploit the non-linear relationship within and across the spatial and diffusion space using non-linear activation, such as ReLU activation, which is otherwise challenging to study and model explicitly.

Practically, the collection of training data is also eased when using the methods described in the present disclosure. To obtain the ground-truth, a longer DTI acquisition with many diffusion-encoding directions (e.g., 90 directions as one example) can be performed and processed (e.g., using eddy current, motion, gradient nonlinearity correction). To obtain the input DWIs, many observations of the set of DWIs can be drawn. For example, for six diffusion-encoding directions and 90 DWIs, approximately 70 observations can be selected with an angle threshold of 10 degrees. Consequently, the training data can be obtained from a few subjects, which in some instances may be only a single subject. Because of the simplicity of the training data collection, the methods described in the present disclosure can be applied to training data acquired on specific scanners from different vendors, hardware (e.g., main field, diffusion-encoding gradient, receive coil) and populations (e.g., sex, age, race, pathology, diseases). In this way, the neural networks can be trained to be hardware-specific, patient population-specific, and so on.

During training, the loss compared to the ground-truth can sometimes be evaluated in brain tissue, excluding the CSF. Because of the high diffusivity of CSF, the diffusion signal in CSF rapidly decays to near zero.

Overall, some implementations of the methods described in the present disclosure suggest transforming the diffusion data to a different representation, such as diffusion tensor elements, spherical harmonics, or ensemble diffusion propagator for the subsequent deep learning. A specific representation optimized for diffusion data can also be automatically learned using unsupervised feature learning.

Figure 7:
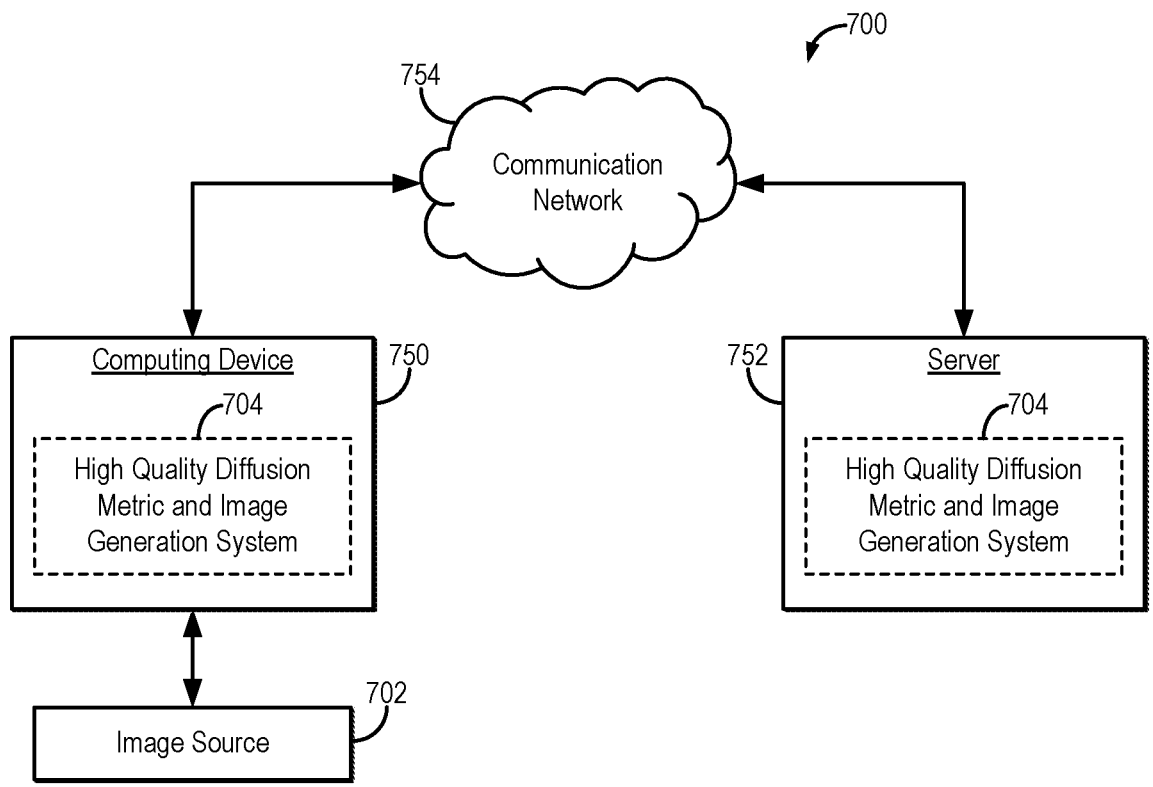
FIG. 7 is a block diagram of an example system for generating diffusion metrics and/or high-quality diffusion-weighted images.

Referring now to FIG. 7, an example of a system 700 for generating diffusion metrics (e.g., scalar and/or orientational diffusion metrics) and/or higher quality diffusion-weighted images in accordance with some embodiments of the systems and methods described in the present disclosure is shown. As shown in FIG. 7, a computing device 750 can receive one or more types of data (e.g., magnetic resonance image data) from image source 702, which may be a magnetic resonance image source. In some embodiments, computing device 750 can execute at least a portion of a diffusion metric and image generation system 704 to generate scalar and/or orientational diffusion metrics and/or higher quality diffusion-weighted images from lower quality magnetic resonance image data received from the image source 702.

Additionally or alternatively, in some embodiments, the computing device 750 can communicate information about data received from the image source 702 to a server 752 over a communication network 754, which can execute at least a portion of the diffusion metric and image generation system 704. In such embodiments, the server 752 can return information to the computing device 750 (and/or any other suitable computing device) indicative of an output of the diffusion metric and image generation system 704.

In some embodiments, computing device 750 and/or server 752 can be any suitable computing device or combination of devices, such as a desktop computer, a laptop computer, a smartphone, a tablet computer, a wearable computer, a server computer, a virtual machine being executed by a physical computing device, and so on. The computing device 750 and/or server 752 can also reconstruct images from the data.

In some embodiments, image source 702 can be any suitable source of image data (e.g., measurement data, images reconstructed from measurement data), such as an MRI system, another computing device (e.g., a server storing image data), and so on. In some embodiments, image source 702 can be local to computing device 750. For example, image source 702 can be incorporated with computing device 750 (e.g., computing device 750 can be configured as part of a device for capturing, scanning, and/or storing images). As another example, image source 702 can be connected to computing device 750 by a cable, a direct wireless link, and so on. Additionally or alternatively, in some embodiments, image source 702 can be located locally and/or remotely from computing device 750, and can communicate data to computing device 750 (and/or server 752) via a communication network (e.g., communication network 754).

In some embodiments, communication network 754 can be any suitable communication network or combination of communication networks. For example, communication network 754 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 754 can be a local area network, a wide area network, a public network (e.g., the Internet), a private or semi-private network (e.g., a corporate or university intranet), any other suitable type of network, or any suitable combination of networks. Communications links shown in FIG. 7 can each be any suitable communications link or combination of communications links, such as wired links, fiber optic links, Wi-Fi links, Bluetooth links, cellular links, and so on.

Figure 8:
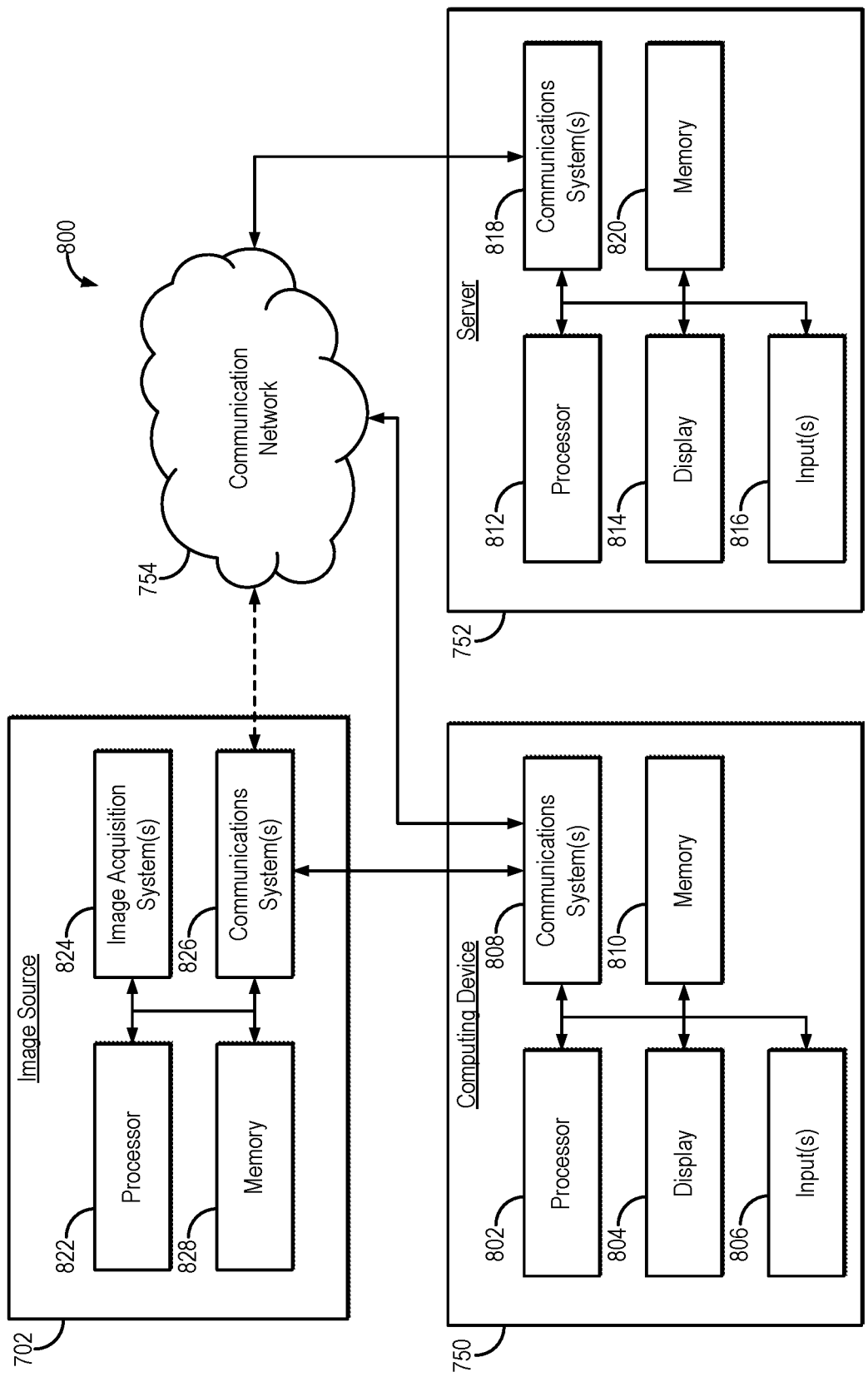
FIG. 8 is a block diagram of example components that can implement the system of FIG. 7.

Referring now to FIG. 8, an example of hardware 800 that can be used to implement image source 702, computing device 750, and server 752 in accordance with some embodiments of the systems and methods described in the present disclosure is shown. As shown in FIG. 8, in some embodiments, computing device 750 can include a processor 802, a display 804, one or more inputs 806, one or more communication systems 808, and/or memory 810. In some embodiments, processor 802 can be any suitable hardware processor or combination of processors, such as a central processing unit ("CPU"), a graphics processing unit ("GPU"), and so on. In some embodiments, display 804 can include any suitable display devices, such as a computer monitor, a touchscreen, a television, and so on. In some embodiments, inputs 806 can include any suitable input devices and/or sensors that can be used to receive user input, such as a keyboard, a mouse, a touchscreen, a microphone, and so on.

In some embodiments, communications systems 808 can include any suitable hardware, firmware, and/or software for communicating information over communication network 754 and/or any other suitable communication networks. For example, communications systems 808 can include one or more transceivers, one or more communication chips and/or chip sets, and so on. In a more particular example, communications systems 808 can include hardware, firmware and/or software that can be used to establish a Wi-Fi connection, a Bluetooth connection, a cellular connection, an Ethernet connection, and so on.

In some embodiments, memory 810 can include any suitable storage device or devices that can be used to store instructions, values, data, or the like, that can be used, for example, by processor 802 to present content using display 804, to communicate with server 752 via communications system(s) 808, and so on. Memory 810 can include any suitable volatile memory, non-volatile memory, storage, or any suitable combination thereof. For example, memory 810 can include RAM, ROM, EEPROM, one or more flash drives, one or more hard disks, one or more solid state drives, one or more optical drives, and so on. In some embodiments, memory 810 can have encoded thereon, or otherwise stored therein, a computer program for controlling operation of computing device 750. In such embodiments, processor 802 can execute at least a portion of the computer program to present content (e.g., images, user interfaces, graphics, tables), receive content from server 752, transmit information to server 752, and so on.

In some embodiments, server 752 can include a processor 812, a display 814, one or more inputs 816, one or more communications systems 818, and/or memory 820. In some embodiments, processor 812 can be any suitable hardware processor or combination of processors, such as a CPU, a GPU, and so on. In some embodiments, display 814 can include any suitable display devices, such as a computer monitor, a touchscreen, a television, and so on. In some embodiments, inputs 816 can include any suitable input devices and/or sensors that can be used to receive user input, such as a keyboard, a mouse, a touchscreen, a microphone, and so on.

In some embodiments, communications systems 818 can include any suitable hardware, firmware, and/or software for communicating information over communication network 754 and/or any other suitable communication networks. For example, communications systems 818 can include one or more transceivers, one or more communication chips and/or chip sets, and so on. In a more particular example, communications systems 818 can include hardware, firmware and/or software that can be used to establish a Wi-Fi connection, a Bluetooth connection, a cellular connection, an Ethernet connection, and so on.

In some embodiments, memory 820 can include any suitable storage device or devices that can be used to store instructions, values, data, or the like, that can be used, for example, by processor 812 to present content using display 814, to communicate with one or more computing devices 750, and so on. Memory 820 can include any suitable volatile memory, non-volatile memory, storage, or any suitable combination thereof. For example, memory 820 can include RAM, ROM, EEPROM, one or more flash drives, one or more hard disks, one or more solid state drives, one or more optical drives, and so on. In some embodiments, memory 820 can have encoded thereon a server program for controlling operation of server 752. In such embodiments, processor 812 can execute at least a portion of the server program to transmit information and/or content (e.g., data, images, a user interface) to one or more computing devices 750, receive information and/or content from one or more computing devices 750, receive instructions from one or more devices (e.g., a personal computer, a laptop computer, a tablet computer, a smartphone), and so on.

In some embodiments, image source 702 can include a processor 822, one or more image acquisition systems 824, one or more communications systems 826, and/or memory 828. In some embodiments, processor 822 can be any suitable hardware processor or combination of processors, such as a CPU, a GPU, and so on. In some embodiments, the one or more image acquisition systems 824 are generally configured to acquire data, images, or both, and can include an MRI system. Additionally or alternatively, in some embodiments, one or more image acquisition systems 824 can include any suitable hardware, firmware, and/or software for coupling to and/or controlling operations of an MRI system. In some embodiments, one or more portions of the one or more image acquisition systems 824 can be removable and/or replaceable.

Note that, although not shown, image source 702 can include any suitable inputs and/or outputs. For example, image source 702 can include input devices and/or sensors that can be used to receive user input, such as a keyboard, a mouse, a touchscreen, a microphone, a trackpad, a trackball, and so on. As another example, image source 702 can include any suitable display devices, such as a computer monitor, a touchscreen, a television, etc., one or more speakers, and so on.

In some embodiments, communications systems 826 can include any suitable hardware, firmware, and/or software for communicating information to computing device 750 (and, in some embodiments, over communication network 754 and/or any other suitable communication networks). For example, communications systems 826 can include one or more transceivers, one or more communication chips and/or chip sets, and so on. In a more particular example, communications systems 826 can include hardware, firmware and/ or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 828 can include any suitable storage device or devices that can be used to store instructions, values, data, or the like, that can be used, for example, by processor 822 to control the one or more image acquisition systems 824, and/or receive data from the one or more image acquisition systems 824; to images from data; present content (e.g., images, a user interface) using a display; communicate with one or more computing devices 750; and so on. Memory 828 can include any suitable volatile memory, non-volatile memory, storage, or any suitable combination thereof. For example, memory 828 can include RAM, ROM, EEPROM, one or more flash drives, one or more hard disks, one or more solid state drives, one or more optical drives, and so on. In some embodiments, memory 828 can have encoded thereon, or otherwise stored therein, a program for controlling operation of image source 702. In such embodiments, processor 822 can execute at least a portion of the program to generate images, transmit information and/or content (e.g., data, images) to one or more computing devices 750, receive information and/or content from one or more computing devices 750, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 9:
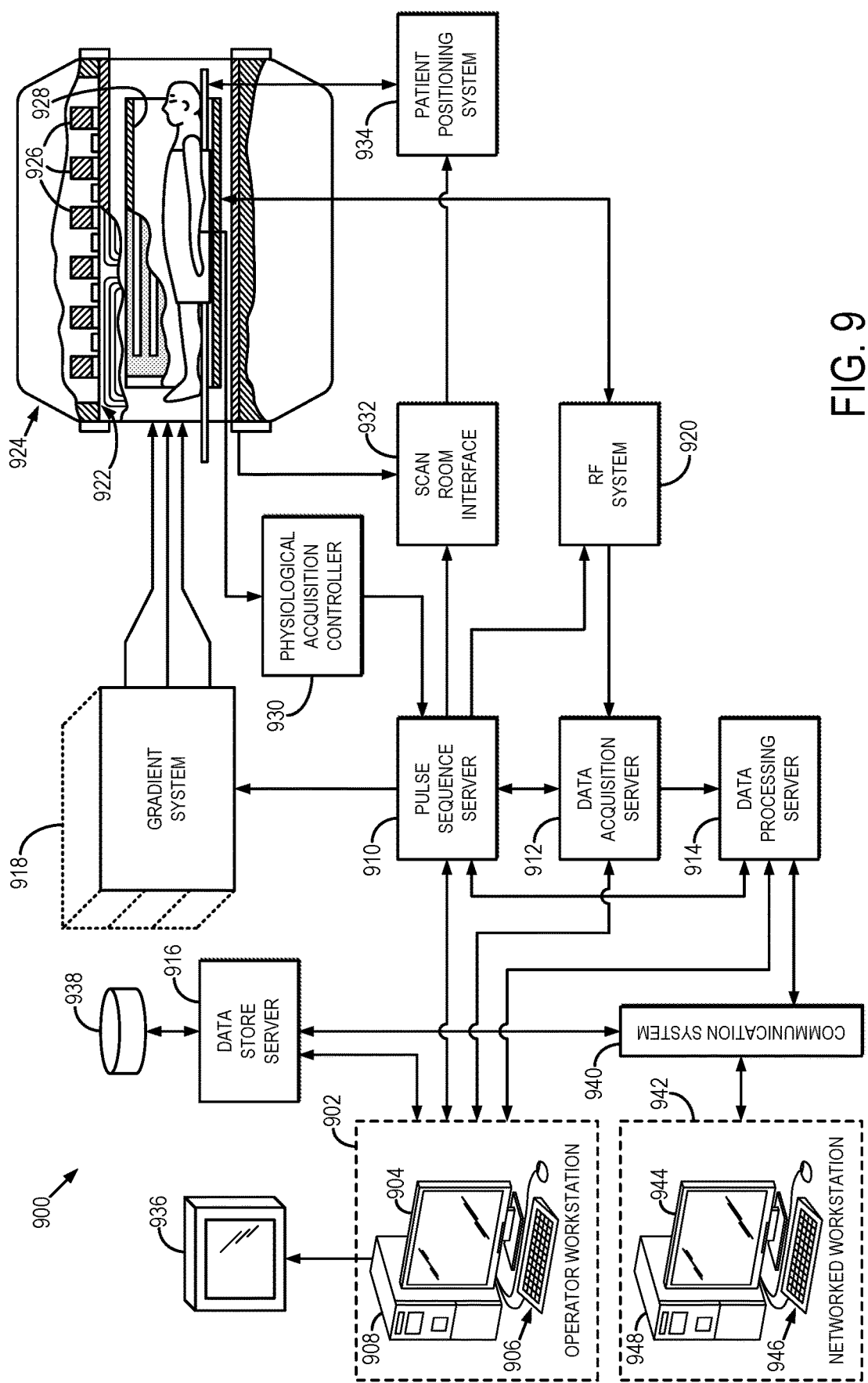
FIG. 9 is a block diagram of an example MRI system that can implement some embodiments described in the present disclosure.

Referring particularly now to FIG. 9, an example of an MRI system 900 that can implement the methods described here is illustrated. The MRI system 900 includes an operator workstation 902 that may include a display 904, one or more input devices 906 (e.g., a keyboard, a mouse), and a processor 908. The processor 908 may include a commercially available programmable machine running a commercially available operating system. The operator workstation 902 provides an operator interface that facilitates entering scan parameters into the MRI system 900. The operator workstation 902 may be coupled to different servers, including, for example, a pulse sequence server 910, a data acquisition server 912, a data processing server 914, and a data store server 916. The operator workstation 902 and the servers 910, 912, 914, and 916 may be connected via a communication system 940, which may include wired or wireless network connections.

The pulse sequence server 910 functions in response to instructions provided by the operator workstation 902 to operate a gradient system 918 and a radiofrequency ("RF") system 920. Gradient waveforms for performing a prescribed scan are produced and applied to the gradient system 918, which then excites gradient coils in an assembly 922 to produce the magnetic field gradients $G_x$, $G_y$, and $G_z$ that are used for spatially encoding magnetic resonance signals. The gradient coil assembly 922 forms part of a magnet assembly 924 that includes a polarizing magnet 926 and a whole-body RF coil 928.

RF waveforms are applied by the RF system 920 to the RF coil 928, or a separate local coil to perform the prescribed magnetic resonance pulse sequence. Responsive magnetic resonance signals detected by the RF coil 928, or a separate local coil, are received by the RF system 920. The responsive magnetic resonance signals may be amplified, demodulated, filtered, and digitized under direction of commands produced by the pulse sequence server 910. The RF system 920 includes an RF transmitter for producing a wide variety of RF pulses used in MRI pulse sequences. The RF transmitter is responsive to the prescribed scan and direction from the pulse sequence server 910 to produce RF pulses of the desired frequency, phase, and pulse amplitude waveform. The generated RF pulses may be applied to the whole-body RF coil 928 or to one or more local coils or coil arrays.

The RF system 920 also includes one or more RF receiver channels. An RF receiver channel includes an RF preamplifier that amplifies the magnetic resonance signal received by the coil 928 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2}; \tag{11}$$

and the phase of the received magnetic resonance signal may also be determined according to the following relationship:

$$\varphi = \tan^{-1}\left(\frac{Q}{I}\right). \tag{12}$$

The pulse sequence server 910 may receive patient data from a physiological acquisition controller 930. By way of example, the physiological acquisition controller 930 may receive signals from a number of different sensors connected to the patient, including electrocardiograph ("ECG") signals from electrodes, or respiratory signals from a respiratory bellows or other respiratory monitoring devices. These signals may be used by the pulse sequence server 910 to synchronize, or "gate," the performance of the scan with the subject's heart beat or respiration.

The pulse sequence server 910 may also connect to a scan room interface circuit 932 that receives signals from various sensors associated with the condition of the patient and the magnet system. Through the scan room interface circuit 932, a patient positioning system 934 can receive commands to move the patient to desired positions during the scan.

The digitized magnetic resonance signal samples produced by the RF system 920 are received by the data acquisition server 912. The data acquisition server 912 operates in response to instructions downloaded from the operator workstation 902 to receive the real-time magnetic resonance data and provide buffer storage, so that data is not lost by data overrun. In some scans, the data acquisition server 912 passes the acquired magnetic resonance data to the data processor server 914. In scans that require information derived from acquired magnetic resonance data to control the further performance of the scan, the data acquisition server 912 may be programmed to produce such information and convey it to the pulse sequence server 910. For example, during pre-scans, magnetic resonance data may be acquired and used to calibrate the pulse sequence performed by the pulse sequence server 910. As another example, navigator signals may be acquired and used to adjust the operating parameters of the RF system 920 or the gradient system 918, or to control the view order in which k-space is sampled. In still another example, the data acquisition server 912 may also process magnetic resonance signals used to detect the arrival of a contrast agent in a magnetic resonance angiography ("MRA") scan. For example, the data acquisition server 912 may acquire magnetic resonance data and processes it in real-time to produce information that is used to control the scan.

The data processing server 914 receives magnetic resonance data from the data acquisition server 912 and processes the magnetic resonance data in accordance with instructions provided by the operator workstation 902. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 914 are conveyed back to the operator workstation 902 for storage. Real-time images may be stored in a data base memory cache, from which they may be output to operator display 902 or a display 936. Batch mode images or selected real time images may be stored in a host database on disc storage 938. When such images have been reconstructed and transferred to storage, the data processing server 914 may notify the data store server 916 on the operator workstation 902. The operator workstation 902 may be used by an operator to archive the images, produce films, or send the images via a network to other facilities.

The MRI system 900 may also include one or more networked workstations 942. For example, a networked workstation 942 may include a display 944, one or more input devices 946 (e.g., a keyboard, a mouse), and a processor 948. The networked workstation 942 may be located within the same facility as the operator workstation 902, or in a different facility, such as a different healthcare institution or clinic.

The networked workstation 942 may gain remote access to the data processing server 914 or data store server 916 via the communication system 940. Accordingly, multiple networked workstations 942 may have access to the data processing server 914 and the data store server 916. In this manner, magnetic resonance data, reconstructed images, or other data may be exchanged between the data processing server 914 or the data store server 916 and the networked workstations 942, such that the data or images may be remotely processed by a networked workstation 942.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a diffusion metric from magnetic resonance image data acquired from a subject, the method comprising:
    (a) accessing magnetic resonance image data with a computer system,
        wherein the magnetic resonance image data comprise:
            a non-diffusion-weighted image acquired from a subject;
            at least six diffusion-weighted images acquired from the subject,
                each diffusion-weighted image corresponding to one of six different diffusion-encoding directions;
    (b) accessing a neural network with the computer system, wherein the neural network has been trained on training data to learn a mapping from lower quality diffusion-weighted images to ground-truth diffusion-weighted images;
    (c) inputting at least the at least six diffusion-weighted images contained in the magnetic resonance image data to the neural network using the computer system, generating output as residual image data that represents image differences relative to the ground-truth diffusion-weighted images;
    (d) generating updated diffusion-weighted images by combining the at least six diffusion-weighted images and the residual image data with the computer system;
    (e) generating a diffusion metric from the updated diffusion-weighted images using the computer system; and
    (f) displaying images of the subject using the diffusion metric.

2. A method for generating at least one of diffusion metrics or diffusion-weighted images of a subject, the method comprising:
    (a) accessing magnetic resonance image data with a computer system,
        wherein the magnetic resonance image data comprise:
            a non-diffusion-weighted image acquired from a subject;
            at least six diffusion-weighted images acquired from the subject,
                each diffusion-weighted image corresponding to one of six different diffusion-encoding directions;
    (b) computing initial diffusion tensor elements from the magnetic resonance image data by using the computer system to fit the magnetic resonance image data to a diffusion tensor model;
    (c) accessing a neural network with the computer system, wherein the neural network has been trained on training data to learn a mapping from lower quality diffusion tensor elements to ground-truth diffusion tensor elements;
    (d) inputting the initial diffusion tensor elements to the neural network using the computer system, generating output as residual diffusion tensor element data that represents diffusion tensor element differences relative to the ground-truth diffusion tensor elements;
    (e) generating updated diffusion tensor elements by combining the initial diffusion tensor elements and the residual diffusion tensor element data with the computer system; and (f) generating at least one of a diffusion metric or a diffusion-weighted image from the updated diffusion tensor elements using the computer system;

(g) displaying at least one of the diffusion metric or a diffusion-weighted image to a user.

3. The method of claim 1, wherein each of the at least six diffusion-weighted images correspond to one of six different diffusion-encoding directions that are optimized to minimize a condition number of a diffusion tensor transformation matrix.

4. The method of claim 1, wherein the neural network is a convolutional neural network.

5. The method of claim 4, wherein the convolutional neural network implements residual learning.

6. The method of claim 1, wherein step (e) comprises generating a scalar diffusion metric.

7. The method of claim 6, wherein the scalar diffusion metric comprises at least one of axial diffusivity, radial diffusivity, mean diffusivity, or fractional anisotropy.

8. The method of claim 6, further comprising generating a diffusion metric map from the scalar diffusion metric, wherein the diffusion metric map depicts a spatial distribution of the scalar diffusion metric within a region of the subject.

9. The method of claim 1, wherein step (e) comprises generating an orientational diffusion metric.

10. The method of claim 9, wherein the orientational diffusion metric comprises an eigenvector.

11. The method of claim 10, wherein the eigenvector is a principal eigenvector and the method further comprises performing tractography based on the principal eigenvector.

12. The method of claim 2, wherein each of the at least six diffusion-weighted images correspond to one of six different diffusion-encoding directions that are optimized to minimize a condition number of a diffusion tensor transformation matrix.

13. The method of claim 2, wherein computing the initial diffusion tensor elements comprises:

generating resampled diffusion-weighted images by resampling the at least six diffusion-weighted images along diffusion-encoding directions that are optimized to minimize a condition number of a diffusion tensor transformation matrix; and computing the initial diffusion tensor elements by fitting the resampled diffusion-weighted imaged and the non-diffusion-weighted image to the diffusion tensor model.

14. The method of claim 2, wherein the neural network is a convolutional neural network.

15. The method of claim 14, wherein the convolutional neural network implements residual learning.

16. The method of claim 2, wherein step (f) comprises generating a scalar diffusion metric.

17. The method of claim 16, wherein the scalar diffusion metric comprises at least one of axial diffusivity, radial diffusivity, mean diffusivity, or fractional anisotropy.

18. The method of claim 17, further comprising generating a diffusion metric map from the scalar diffusion metric, wherein the diffusion metric map depicts a spatial distribution of the scalar diffusion metric within a region of the subject.

19. The method of claim 2, wherein step (f) comprises generating an orientational diffusion metric.

20. The method of claim 19, wherein the orientational diffusion metric comprises an eigenvector.

21. The method of claim 20, wherein the eigenvector is a principal eigenvector and the method further comprises performing tractography based on the principal eigenvector.

22. The method of claim 2, wherein step (f) comprises generating one or more high-quality diffusion-weighted images that have a higher quality that the diffusion-weighted images contained in the magnetic resonance image data.

23. The method of claim 22, wherein generating the one or more high-quality diffusion-weighted images comprises applying an inverse diffusion tensor transformation to the updated diffusion tensor elements.

* * * * *

UNITED STATES PATENT AND TRADEMARK OFFICE
CERTIFICATE OF CORRECTION

| | | |
|---|---|---|
| PATENT NO. | : 11,874,359 B2 | Page 1 of 1 |
| APPLICATION NO. | : 17/442817 | |
| DATED | : January 16, 2024 | |
| INVENTOR(S) | : Qiyuan Tian et al. | |

It is certified that error appears in the above-identified patent and that said Letters Patent is hereby corrected as shown below:

In the Specification

Column 1, Line 23, "N5096056" should be --NS096056--.

Signed and Sealed this
Ninth Day of April, 2024

Katherine Kelly Vidal
*Director of the United States Patent and Trademark Office*